United States Patent [19]

Love et al.

[11] Patent Number: 4,828,799

[45] Date of Patent: May 9, 1989

[54] THERAPEUTIC DRUG MONITORING AND ANALYTE DETERMINATION UTILIZING MICELLAR CHROMATOGRAPHY

[75] Inventors: Linda J. C. Love, Mountainside, N.J.; Robert Weinberger, Chappaqua, N.Y.

[73] Assignee: Research Corporation, New York, N.Y.

[21] Appl. No.: 749,157

[22] Filed: Jun. 26, 1985

[51] Int. Cl.$^4$ .................. G01N 30/02; G01N 33/48
[52] U.S. Cl. .................. 422/70; 422/68; 436/161; 436/901; 436/63
[58] Field of Search .............. 436/63, 161, 162, 8–18; 435/501, 527, 805, 810; 422/61, 68–70

[56] References Cited

U.S. PATENT DOCUMENTS

| | | | |
|---|---|---|---|
| 3,713,779 | 1/1973 | Sirago et al. | 436/901 |
| 4,560,649 | 12/1985 | Saxena et al. | 436/501 |
| 4,703,004 | 10/1987 | Hopp et al. | 435/68 |

OTHER PUBLICATIONS

Miles & Hales, *Labelled Antibodies and Immunological Assay Systems*, 219 Nature 186–89 (1968).
Yarmchuk, et al., *Selectivity in Liquid Chromatography with Micelle Mobile Phases*, 54 Anal. Chem. 2233–38 (1982).
Armstrong & Stine, *Evaluation and Perturbation of Micelle-Solute Interactions*, 105 J. Am. Chem. Soc. 6220–23 (1983).
Armstrong & Stine, *Selectivity in Pseudophase Liquid Chromatography*, 55 Anal. Chem. 2317–20 (1983).

Primary Examiner—Barry S. Richman
Assistant Examiner—T. J. Wallen
Attorney, Agent, or Firm—Scully, Scott, Murphy & Presser

[57] ABSTRACT

A method for the determination of the drug or other analyte content and concentration in bodily fluids that are directly injected in a micellar chromatographic column. Various embodiments of kits are also disclosed.

12 Claims, 6 Drawing Sheets

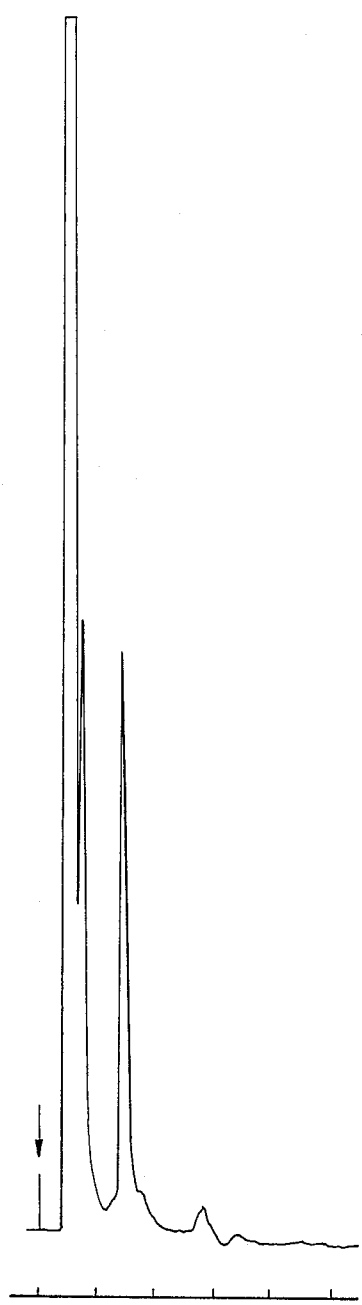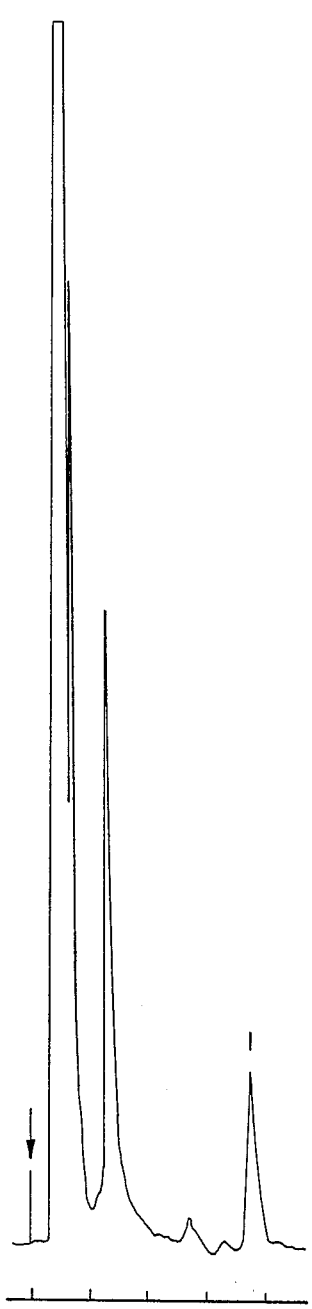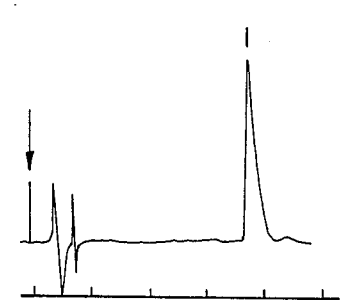
TIME (MIN)
FIG.3A
TIME (MIN)
FIG.3B
TIME (MIN)
FIG.3C

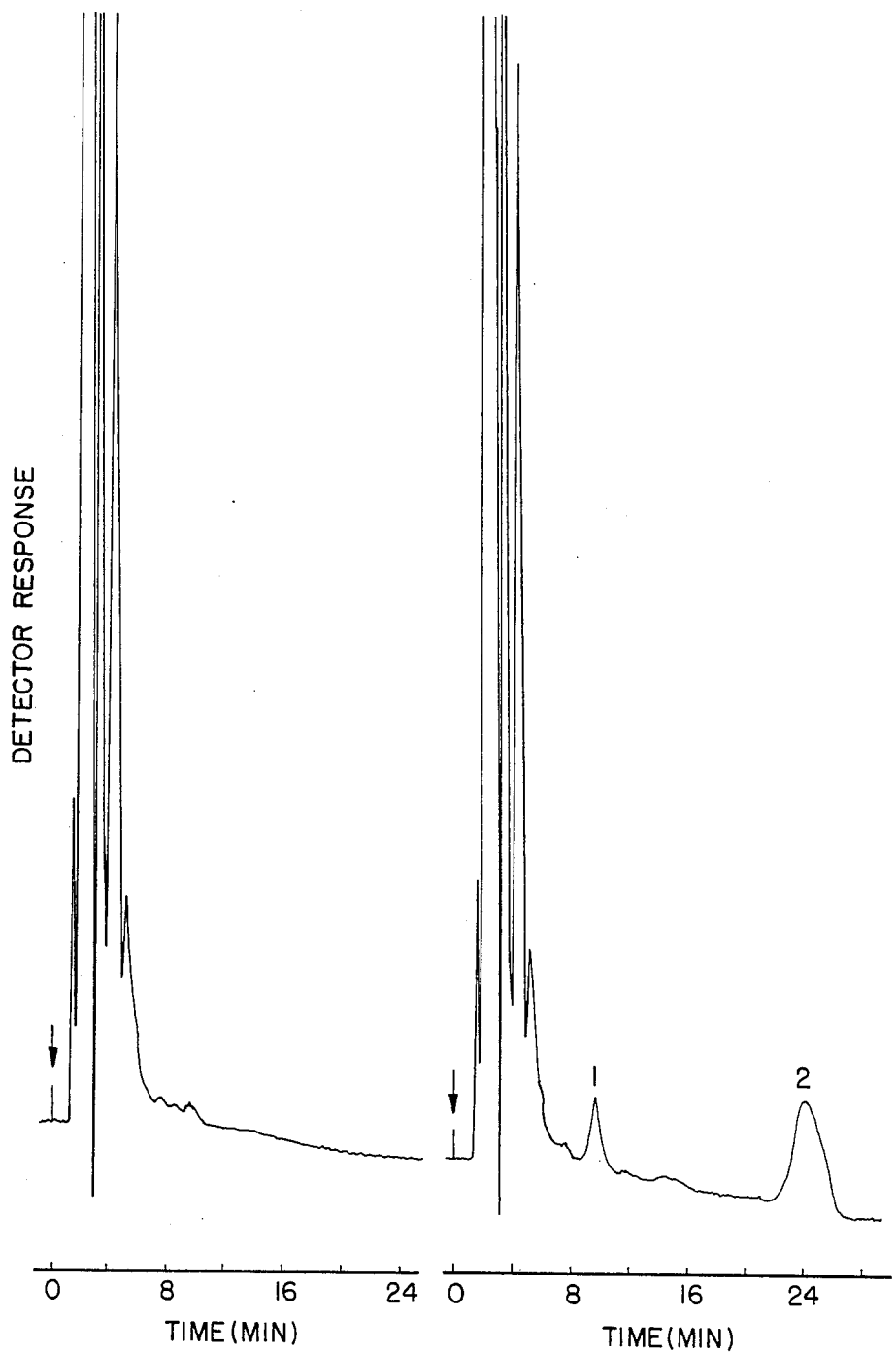

THERAPEUTIC DRUG MONITORING AND ANALYTE DETERMINATION UTILIZING MICELLAR CHROMATOGRAPHY

GOVERNMENT SUPPORT

The invention described herein was made in the course of work under a grant or award from the National Science Foundation (Grant No. CHE-8216878).

BACKGROUND OF THE INVENTION

1. Field of the Invention

This invention relates to a method of determining drug levels of body fluids by micellar chromatography. More specifically, this invention relates to the determination of the concentrations of drugs in bodily fluids, i.e. serum or urine by direct injection into a micellar chromatographic column.

2. Discussion of the Prior Art

Therapeutic drug monitoring has shown rapid growth recently due to the development of specific and sensitive assays for minute quantities of drugs in various body fluids. In addition, therapeutic drug monitoring has become an essential part of many hospital clinician's work, i.e. physicians, medical technicians and nurses.

Normally, therapeutic drug monitoring is considered when several of the following conditions exist: (1) there is a question of patient compliance, (2) there is a lack of therapeutic effect, (3) the drug has a narrow therapeutic range, (4) there is a danger of toxicity and (5) there is a need for medico-legal verification of treatment.

Various techniques are used in therapeutic drug monitoring, such as, radioimmunoassay, flourescence immunoassays and enzyme-multiplied immunoassay techniques. Additionally, chromatographic methods such as thin layer chromatography, gas-liquid chromatography and high performance liquid chromatography are widely used.

The use of radioimmunoassay techniques for therapeutic drug and toxic drug level monitoring remains the most popular technique. Foremost among these are the Abuscreen kits, which are illustrated by the barbiturate test kit. The Abuscreen radioimmunoassay kit for barbiturates is based on the competitive binding to an antibody of radiolabeled antigen and unlabeled antigen in proportion to their concentration in the solution. Unlabeled antigen displaces radioactive antigen from the antibody present. An unknown specimen is added to a test tube containing known amounts of barbiturate antibodies and radiolabeled antigen. After precipitation and centrifugation, the supernatant fluid, which contains the free antigen, is transferred to test tubes for counting in a gamma scintillation counter. A positive specimen is identified qualitatively when the radioactivity is equal to or greater than that of the positive control and quantitatively by comparison to a standard curve. These radioimmunoassay techniques have been applied to various drugs including morphine, cocaine, amphetamine, methadone hydrochloride, and phencylidine phenol among others.

As noted, up to the present time, the radioimmunoassay (RIA) method in its various forms has been the most sensitive system available. The RIA method, unfortunately, has several serious disadvantages, including the requirement of special equipment, trained staff, the recited need for extra safety measures to protect against harmful radiation, special licensing, controlled radioactive waste disposal and the continuous disappearance of labeled compound by radioactive decay. The possibility of replacing the radioactive label with an enzyme label was proposed in 1968 in an article by L. E. M. Miles and C. N. Hales, entitled "Labelled Antibodies and Immunological Assay Systems", Lancet, II, 492 (1968), and Nature 219, 168 (1968). No procedural details were provided; the article offered only the general idea, leaving it to future workers to determine the basic step and to perform the extensive experimentation needed to establish a practical operative enzymatic immunoassay method.

Various chromatographic techniques have been utilized for different types of therapeutic drug monitoring. For example, thin layer chromatography is used to screen urine specimens for drugs of abuse. Many prepackaged kits are available for this purpose; the kits contain plates, sprays, applicators, and reference tables for determining color reactions and $R_f$ (distance ratio) values for the compounds of interest. The most common drugs screened with this type of procedure are salicylates, barbiturates, opiates, pentachlorophenol, benzodiazepines and amphetamines. It is recommended that positive results obtained should be verified with other methodologies. A urine sample is extracted with an organic solvent and a concentrated aliquot is applied in a small spot to a thin layer chromatography plate which is coated with cellulose or another coating material. The plate with the dried spots is immersed in a tank containing a mobile phase, the mobile phase moves up the thin layer chromatography plate by capillary action, and the constituents of the mixture contained in the spot are carried across the plate with the mobile phase. In transit, they partition between the solvent and the particles of the coating. The partition retards some constituents and allows others to move more rapidly in comparison with the solvent front. The plate is dried after the solvent has moved a sufficient distance up the plate. A series of sprays are applied and characteristic colors of the mobilities are observed for compounds of interest.

A publication by Paul Yarmchuk, et al., entitled "*Selectivity in Liquid Chromatography with Micellar Mobile Phases*" in Anal. Chem. 1982, Vol. 54, 2233–2238 describes the use of micellar mobile phases to control selectivity in liquid chromatography. The study compared two surfactants which form comparable micelles differing only in the nature of the polar head groups. The surfactants studied were sodium lauryl sulfate and dodecyltrimethylammonium bromide. Results of the study illustrated that selectivity can be enhanced by proper choice of surfactant type and mobile phase concentration.

Another publication by Daniel W. Armstrong, et al., entitled "*Evaluation and Pertubation of Micelle-Solute Interactions*", J. Am. Chem. Soc., 1983, Vol. 105, pp. 6220–6223 describes the interaction of seven compounds with sodium dodecyl sulfate micelles using LC and TLC. Results of the study illustrated that the solute-micelle interaction can be classified as binding, nonbinding, or antibinding.

A publication by Daniel W. Armstrong, et al., entitled "*Selectivity in Pseudophase Liquid Chromatography*", Anal. Chem., Vol. 55, pp. 2317–2320 describes the pseudophase liquid chromatographic separation for fourteen compounds by using anionic micellar mobile phase. The study discussed the different characteristics of the compounds using the pseudophase liquid chromatography.

While the art has provided various methods for therapeutic drug monitoring, the need still exists for a method of therapeutic drug monitoring that is accurate and utilizes more sensitive chromatographic techniques. For example, present chromatographic methods generally require separation of the drug from the serum's protein base before analysis. This preparation step involves tedious and time consuming extraction procedures and/or protein precipitation steps. Accordingly, it is one object of the present invention to provide a novel method of therapeutic drug monitoring utilizing chromatographic methods.

Another object of the present invention herein is to provide a new method of therapeutic drug monitoring utilizing micellar chromatography.

A further object of this invention is to provide a new method of therapeutic drug monitoring that allows direct injection of a bodily fluid into a chromatographic column.

Still another object of this invention is to provide a new method of determining the concentration and identifying analytes in a bodily fluid utilizing micellar chromatography.

A still further object of this invention is to provide an improved method of therapeutic drug monitoring that involves direct injection of body fluids without any preparation or extraction of the sample.

The achievement of these and other objects will be apparent from the following description of the subject invention.

SUMMARY OF THE INVENTION

These and other objects are achieved by eluting a bodily fluid in a chromatographic column and determining the content and concentration of drugs found in the sample. Briefly, this invention relates to therapeutic drug monitoring utilizing a chromatographic column composed of an anionic, cationic, zwitterionic, or nonionic micelle as the mobile phase of the column. Specifically, this invention relates to a method for the determination of the concentration of drugs or other analytes in bodily fluids which comprises:

(a) injecting a bodily fluid into a micellar chromatographic column containing an anionic, cationic, zwitterionic, or nonionic surfactant as the mobile phase at a concentration at or above the critical micelle concentration; and (b) detecting said eluting bodily fluid to produce a chromatogram.

In another embodiment, this invention relates to a kit useful for the determination of the drug concentration or analyte concentration in a bodily fluid which comprises:

a carrier being compartmentalized to receive one or more container means in close confinement therein;

a first container means comprising a surfactant as a component for preparation of a mobile phase for chromatographic analysis;

a second container means comprising a solvent for adding to the surfactant for preparation of the mobile phase;

a third container means comprising a known drug or other analyte standards in the appropriate body fluid at predetermined values for standardization of a chromatographic column, a fourth container means comprising a standard blank of the appropriate body fluid for calibration of the chromatographic column; and a fifth container means comprisng the appropriate organic modifiers for preparation of a mobile phase;

a sixth container means comprising the appropriate inorganic modifiers for preparation of a mobile phase;

a seventh container means comprising pH adjustment materials;

an eighth container means comprising the appropriate chromatographic column;

a packet with instructions for the preparation of the mobile phase and calibration of the chromatographic column for the determination of the contents and concentration of the sample.

BRIEF DESCRIPTION OF THE DRAWINGS

FIGS. 3A, 3B and 3C are chromatograms of a serum blank, serum with added chloramphenicol, respectively, and water with added chloramphenicol.

FIGS. 4A and 4B are chromatograms of a urine blank (A) and urine with added propanolol and quinidine, respectively (B).

DETAILED DESCRIPTION OF THE INVENTION

Figure 1:
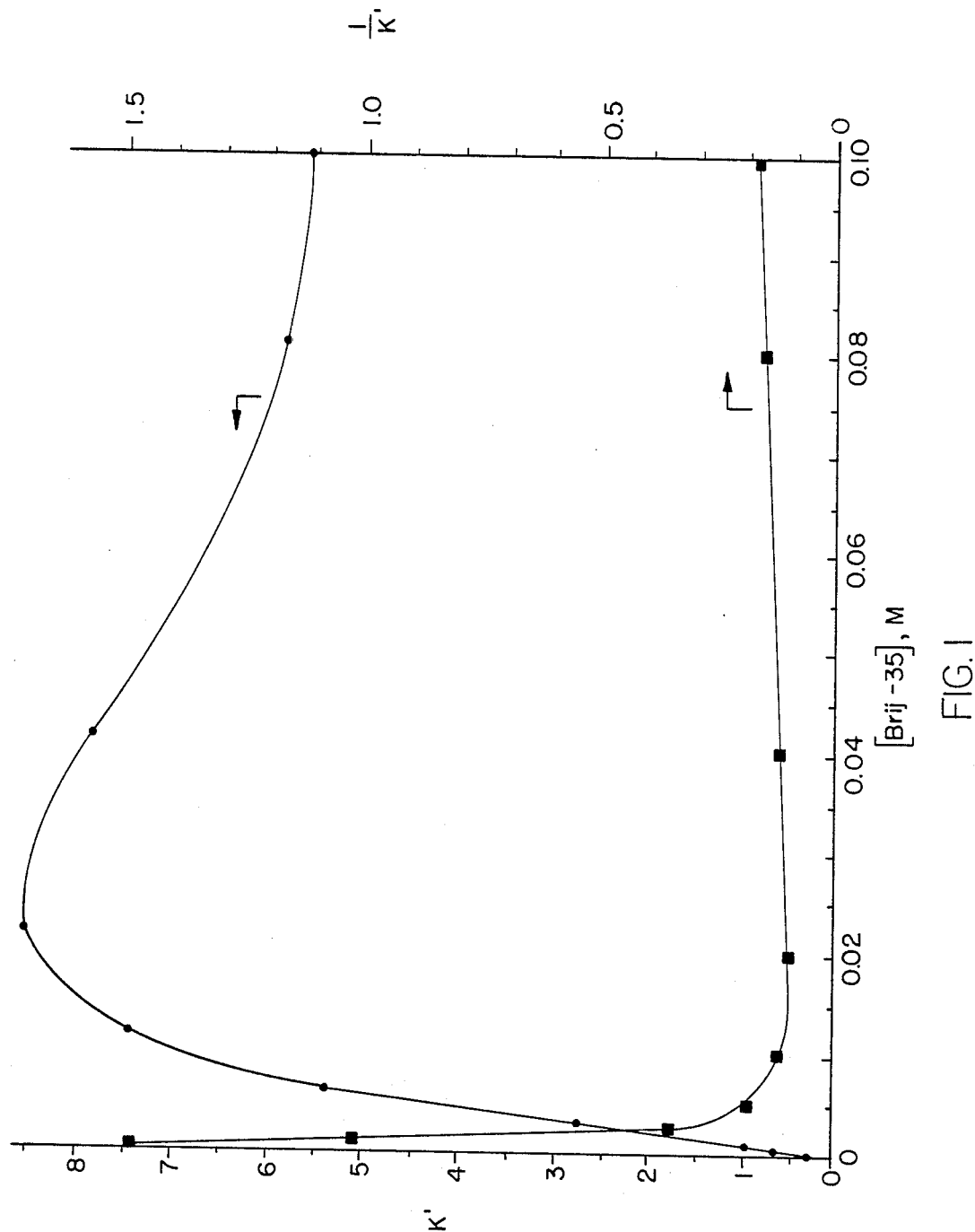
FIG. 1 is a chart illustrating the dependence of k' and 1/k' on the concentration of Brig-35 for 2-naphthalenesulfonic acid.

This invention relates to a method of therapeutic drug monitoring and analyte determination utilizing micellar chromatography. Specifically, this invention is directed to the direct injection of serum, urine or other bodily fluids into the chromatographic column for therapeutic drug monitoring and analyte determination.

Therapeutic drug monitoring and analyte determination utilizing chromatography has been widely used by clinicians. However, such methods require that the specimen undergoes some extraction or preparation prior to utilization of any specific chromatographic techniques. The extraction or preparation of the specimen was necessary to prevent protein precipitation or column clogging. The extraction or preparation is generally a tedious or time consuming process that renders the technique impractical for hospital use or other clinical uses.

High performance liquid chromatography can be broken down into four major areas: (1) liquid-solid chromatography, (2) partition chromatography, (3) ion-exchange, and (4) exclusion chromatography. In addition, partition chromatography can be subdivided into normal and reverse phase.

The chromatographic technique utilized in the present invention is reverse phase partition chromatography or more specifically, micellar chromatography.

Micellar chromatography can be characterized by the partitioning of a solute between: (1) the bulk water and the micelle, (2) the bulk water and the stationary phase, and (3) the micelle and the stationary phase.

The ability to monitor the concentrations of a drug is based on the pharmacokinetic description of the action of the drug. Thus drug monitoring is based on the following principles and assumptions: (1) the drug exerts its effect by interacting with receptor sites in tissues of organs, (2) the drug is carried to the receptor sites by the blood, and (3) the concentration of the drug in the vicinity of the receptor sites is proportional to the concentration of the drug in the blood and determines the intensity of the response. Thus, for systematically acting drugs, the time course of the drug in the blood stream determines the onset, duration, and intensity of both beneficial and adverse effects. Therefore, by adjusting drug dosages to maintain the blood drug concentration within a therapeutic range, the patient derives more benefit than would be possible by clinical judgement alone.

Therapeutic drug monitoring and analyte determination through direct injection of bodily fluids utilizing micellar chromatography has unexpectedly been found to be possible without prior bodily fluid preparation. This new method avoids the deficiencies of the prior art, such as protein precipitation and column clogging. Bodily fluids contemplated to be within the scope of this invention are saliva, serum, urine, whole blood, phelgm, mucous, cerebrospinal fluid, pertioneal fluid, embryonic fluid, semen, vaginal or cervical secretions and the like. Although not a fluid, feces may be analyzed by the process of this invention and for purposes of this disclosure and the claims feces shall be considered to be within the scope of the term "bodily fluids" as it is used herein.

The mobile phase can be prepared from any anionic, cationic, zwitterionic, or nonionic surfactant. For example, surfactants contemplated to be within the scope of this invention are sodium dodecyl sulfate, polyoxyethylene (23) dodecyl (Brij-35), docecyltrimethylammonium bromide, and N,N-dimethyl-N- (carboxymethyl)octylammonium salt, with sodium dodecyl sulfate and Brij-35 being preferred.

A quantitative equilibrium-based model that relates experimental chromatographic behavior of neutral solutes to the concentration of sodium dodecyl sulfate micelles in the mobile phase is represented as follows:

$$K' = \frac{\phi [L_s] K_1}{1 + K_2 [M_m]}$$

where k' is the capacity factor of injected solute, $\phi$ is the ratio of the volume of the stationary phase $v_s$ to the volume of the mobile phase $v_m$ in the column, $[L_s]$ is the molar concentration of stationary phase sites, $K_1$ is the solute-stationary phase equilibrium constant, and $K_2$ is the equilibrium constant between the solute per monomer of surfactant in the micelle. The term $[M_m]$ is the molar concentration of surfactant in the micelle in the mobile phase as defined by formula $[M_m]$=[surfactant]$-$CMC. Consequently, the equation demonstrates that the concentration of the mobile phase can profoundly affect the retention time of a given sample.

For ionizable solutes such as weak organic acids, the additional prototropic equilibria affecting micelle-solute association and chromatographic partitioning must be considered. The interaction of undissociated HA, and the dissociated form, A-, with the stationary phase, $L_s$, and the surfactant in the micelle, $M_m$, forming complexes $HAL_s$, $HAM_m$, $AL_s^-$, and $AM_m^-$, are represented by equations 1-7 where the species molar concentrations in the two phases are denoted by subscripts s and m.

$$HA + L_s \rightleftharpoons HAL_s \qquad (1)$$

$$HA + M_m \rightleftharpoons HAM_m \qquad (2)$$

$$A^- + L_s \rightleftharpoons AL_s^- \qquad (3)$$

$$A^- + M_m \rightleftharpoons AM_m^- \qquad (4)$$

$$HAM_m + L_s \rightleftharpoons HAL_s + M_m \qquad (5)$$

$$AM_m^- + L_s \rightleftharpoons AL_s^- + M_m \qquad (6)$$

$$HA \rightleftharpoons A^- + H^+ \qquad (7)$$

The equilibrium constants corresponding to Eqs. 1–6 are $K_1$ to $K_6$, and $K_{am}$ represents the apparent acid dissociation constant of HA in micellar solution (Eq. 7). Equations 5 and 6, representing the direct transfer of solute in the micelle to the stationary phase, may be neglected ($K_5 \times K_2 = K_1$, and $K_6 \times K_4 = K_3$). $[M_m]$ is calculated by $[M_m]$=[surfactant]$-$CMC, where CMC is the critical micelle concentration. This model calculates equilibrium constants, not partition coefficients, and has the advantages over other models that the volume of the stationary phase, $v_s$, and the partial specific volume of the surfactant, $\bar{v}$, need not be known. Significantly, if micelle-solubilizate equilibrium constants are available from independent sources, the model can predict chromatographic behavior of neutral species at any concentration of micelles and at any pH.

For intermediate pH values, an equation relating capacity factor to pH, where $k_o'$ is the capacity factor for neutral solutes and acid solutes at low pH and $k_1'$ is the capacity factor for these dissociated forms of acid solutes at high pH.

$$K' = \frac{k_o' (1 + K_2[M_m]) + k_1' (1 + K_4[M_m]) K_{am}/[H^+]}{1 + K_2[M_m] + (1 + K_4[M_m]) K_{am}/[H^+]} \qquad (8)$$

A similar equation can be derived for the interaction of weak organic bases by replacing HA and A-- with the protonated base BH+, and free base form, B, into Eqs. 1–9. The equation relating capacity factor to pH for weak organic bases follows.

$$K' = \frac{k_1' (1 + K_2[M_m]) + k_o' (1 + K_4[M_m]) K_{am}/[H^+]}{1 + K_2[M_m] + (1 + K_4[M_m]) K_{am}/[H^+]} \qquad (9)$$

where $k_o'$ is the limiting capacity factor of neutral base, B, $k_1'$ is the limiting capacity factor of protonated BH+form, and $K_{am}$ is the apparent acid dissociation constant of the protonated weak organic base, BH+.

If $[M_m]$ is constant, Eqs. 8 and 9 predict a sigmoidal-type dependence of k' on pH, and if the pH is constant, they predict parabolic curve dependence of k' on $[M_m]$. For each solute, the three parameters of this model, ($k_o'$, $k_1'$, and $K_{am}$), can be estimated from experimental data obtained by measuring solute capacity factor versus mobile phase pH, and these values can be used to calculate k' values for organic acids and bases at different pHs.

Critical micelle concentration for purpose of the present invention is defined as the concentration of a surfactant (an amphiphilic molecule which is charged or polar) at which aggregation of the surfactant molecules or ions occurs to form assemblies, known as micelles, as evidenced by abrupt changes in various physical properties such as surface tension, solute solubilization, electrical conductivity, etc.

The concentration of the mobile phase should be in a range of about 1.01 times the critical micelle concentration of the surfactant to 0.99 times the Krafft point of the surfactant. The preferred range should be about the critical micellar concentration of the surfactant to about (0.9) times the Krafft point. Subsequent to thorough mixing, the solution is filtered through a membrane filter with a thickness in the range of about 0.2 um to about 0.5 um, with a thickness of about 0.45 um being preferred. The solution is then degassed under vacuum conditions for about 10 minutes to about 40 minutes, with the preferred time being about 20 minutes.

The ability of ionizable acids and bases to interact with micelles or to interact with nonpolar stationary phases can be affected by altering the pH of the mobile phase. Buffers added to the mobile phase not only maintain a constant pH, but can also improve efficiency, enhance resolution, improve asymmetric peaks and minimize other undesirable phenomena. The choice of the pH value to employ is dictated by the $pK_a$ or $pK_b$ of the individual analytes, such as for example, acetosalicyclic acid using nonpolar column stationary phases. It is believed that at mobile phase, pH values larger than the analyte's $pK_a$, the peak for this particular drug is not evident and that the anionic solute probably elutes with the serum or other bodily fluid components. It is also thought that an appreciable amount of the surfactant is adsorbed onto nonpolar column packing. Consequently, both hydrophobic and electrostatic interactions can occur with the stationary phase and with the micellar assembly, especially for ionizable molecules. Thus, pH of the micellar phase must be adjusted, when ionizable drugs are to be analyzed. The pH of the micellar phase can be in the range of about 1 to about 14, with the preferred range of about 2 to about 7. The pH can be adjusted by the addition of an appropriate amount of a buffer such as for example, acetate buffer, phosphate buffer, carbonate buffer, borate buffer, or by addition of appropriate acids or bases. The concentration and amount of the buffer will depend on the column type and surfactant used to prepare the mobile phase as well as the drug or other analytes assayed. Any known method of adjusting the pH is contemplated to be within the scope of this invention.

The primary equilibria generally recognized to be important in micellar chromatography are those of the solute between the bulk water and the micelle aggregate, $K_2$ and of the solute between the bulk water and the stationary phase, $K_1$. Bulk phase water in these systems acts as a barrier through which the solute must pass, and it slows down mass transfer between the micelles and the stationary phase. The key to improving the efficiency of separation is to reduce the water barrier by addition of organic modifiers, or to increase the mass transfer rate constants by other means such as elevated temperature, reduced flow rate, and/or reduced micelle concentration.

Organic modifiers, such as propanol, present in the micellar mobile phase increase chromatographic efficiency by wetting the hydrophobic stationary phase surface and, thus, promoting transfer from the aqueous phase. They also blend with the bulk water phase, making it less polar, allowing nonpolar solutes to more rapidly exit the micellar assembly and desorb from the stationary phase, thereby improving efficiency. Organic modifiers must not adversely alter the micelle characteristics which provide the distinct advantage of selectivity afforded by micellar chromatography. If they only alter kinetic and thermodynamic processes, and do not damage the integrity of the micellar aggregate, then improved efficiency can be achieved with no loss in selectivity. Selectivity for certain compounds can also be improved by using detection schemes other than absorption or fluorescence, such as room temperature phosphorescence, sensitized room temperature biacetyl phosphorescence, electrochemical or refractive index.

Various organic modifiers can be used to increase efficiency and selectivity of the mobile phase. Organic modifiers contemplated to be within the scope of this invention are any $C_1$ to $C_8$ alcohols and acetonitrile, with propanol, methanol and acetonitrile being preferred. The organic modifier is added to the mobile phase in a concentration of about 0% to about 40% of the total volume by weight of the mobile phase with the preferred range being about 2% to about 15% of total volume by weight of the mobile phase. For example, the effect of 10% propanol in a 0.08 M sodium dodecyl sulfate mobile phase is shown in the separation of quinine and quinidine alkaloids in directly injected blood serum. The two solutes are diastereoisomers and are eluted at the same time at all concentration of aqueous SDS mobile phase employed. However, addition of 10% propanol to the SDS mobile phase results in good baseline separation. This indicates that propanol not only can enhance sensitivity by improving efficiency, but also can enhance selectivity. Generally, other organic modifiers such as acetonitrile, 2-propanol, and methanol, can be used with similar results, although propanol gave better selectivity. The longer hydrocarbon chain of propanol may be incorporated into the micelle forming comicelles, and it can more effectively reduce the polarity of the bulk water phase, both of which should facilitate mass transfer.

The flow rate of the chromatographic column which thereby affects the retention time of the sample in the column can be adjusted for an efficient analysis depending on the type of sample being analyzed. For example, certain classes of samples will have a prolonged retention time within the column because of their ionic characteristics. In order to avoid this problem, the flow rate can be adjusted in order to minimize the retention time and provide an efficient means of analyzing the sample. The flow rate can be adjusted in the range of about 10 $\mu$l/min to about 20 ml/min, with the preferred range of about 0.5 ml/min. to about 4 ml/min with conventional high performance liquid chromatography.

With fluorescence detection an improvement in the signal to noise ratio and therefore, in sensitivity can result by selection of an optimum excitation wavelength and an emission cutoff filter. The optimum excitation wavelength is dependent on the analyte being assayed, with the preferred values generally being equal to or near the analyte's absorption maximum wavelength. The emission cutoff filter used in the fluorometric detector is dependent on the analyte being assayed, with the preferred value generally being one that transmits the largest emission signal with the least amount of interfering background.

Various classes of drugs and analytes are envisioned to be within the scope of this invention. The method of therapeutic drug monitoring and analyte determination is intended to be for conventional drug monitoring and analyte determination such as, for example, theophylline, digoxin and the like, as well as for illicit drugs such as cocaine, cannabis and the like. Further, any chemical absorbed or ingested or otherwise present in a bodily fluid is intended to be within the scope of this invention. The present invention contemplates no special preparation of the bodily fluid prior to direct injection into the chromatographic column. However, simple procedures known to a skilled artisan can be preformed to enhance the efficiency and selectivity of the present invention. For example, separating whole blood into its serum and red cell components or centrifuging a urine specimen may be advantageous.

In an alternate embodiment of the present invention, a kit for therapeutic drug monitoring and analyte determination kit is contemplated to be within the scope of this invention. For example, a kit would contain all of necessary reagents, materials and instructions for preparation of the mobile phase. Additionally, the kit would contain the necessary known drug samples, controls and instructions to calibrate the column in order to determine an unknown specimen.

The following examples are presented as specific embodiments of the present invention which show some of its unique characteristics, but are not to be considered as constituting a limitation on the present invention.

EXAMPLE 1

Apparatus

The high performance liquid chromatography system consisted of a Fast.LC high pressure pump (Technicon, Inc., Tarrytown, NY), a LDC UV monitor detector (254 nm) (Laboratory Data Control, Rivera Beach, FL), and a Model FS970 LC fluorometer (Kratos Instruments, Ramsey, NJ). The columns were 5 um Supelcosil CN (15cm×4.6 mm i.d. and 25cm×4.6 mm i.d.). and a 10 μm u-Bondapak C-18 (30cm×3.9 mm i.d.) (Waters Associates, Milford, MA). A precolumn (12.5mm×4.6mm i.d.) (Whatman, Inc., Clifton, NJ) packed with silica gel 25–40 μm) (Whatman, Inc.) was located between the pump and the sample injector to saturate the mobile phase with silica to minimize dissolution of the analytical column packing. A model 5000 Fisher strip chart recorder was used to record the chromatograms.

Reagents

Electrophoresis grade sodium dodecyl sulfate obtained from Bio-rad, Inc. (Rockville Centre, NY), and polyoxyethylene(23)dodecyl (Brij-35) from Sigma Chemical Co., St. Louis, MO), were used as received. Serum blank samples and the analytes acetaminophen, phenobarbital, chloramphenicol, and propanolol were obtained from the General Diagnostics Division of Warner Lambert (Morris Plains, NJ), quinine from Mallinckrodt (St. Louis, MO), quinidine from S. B. Penic Co. (Lyndhurst, NJ), and 2-naphthalene sulfonic acid from J. T. Baker. All other reagents such as solvents and sodium acetate were obtainer from Fisher Scientific Co., (Springfield, NJ), and the water was steam distilled. All solutes and other reagents were used as received.

Procedure

Micellar mobile phases were prepared by dissolving the appropriate amount of surfactant in distilled water or 0.05 M sodium acetate buffer containing the specified amount of organic modifier, followed by filtration through a 0.45 μm Nylon-66 membrane filter (Rainin Instruments, Woburn, MA), and degassing under vacuum prior to use. Methanolic stock solutions of eluates were diluted to the desired concentrations with distilled water or dilute methanol. For direct serum injection, aliquots of the stock solutions were diluted with blank serum, and these serum standards were injected directly into the LC system.

A 20 μl sample of 2-naphthalenesulfonic acid was injected by means of a sample injector into the chromatographic apparatus. The flow rate of the fast LC high pressure pump was set at 2.0 ml/min. and polyoxyethlene (23) dodecyl (Brij-35) was used in the preparation of the mobile phase. FIG. 1 illustrates the elution behavior of 2-naphthalenesulfonic acid. At concentration greater than the critical micellar concentration, but less than 0.02 M, electrostatic repulsing effects dominated over hydrophobic attraction, which caused an increase in the capacity factor (expulsion of the anionic solute from the mobile phase). As the surfactant concentration approached 0.02 M, the two opposing forces tended to balance one another, slowing the rate of increase in $k'$ as 2-naphthalenesulfonic acid tended to solubilize into or onto the micellar assemblies. The much less polar nonionic micelle exhibited less columbic repulsion and can associate with negative solutes over certain micelle concentration ranges.

EXAMPLE 2

Figure 2:
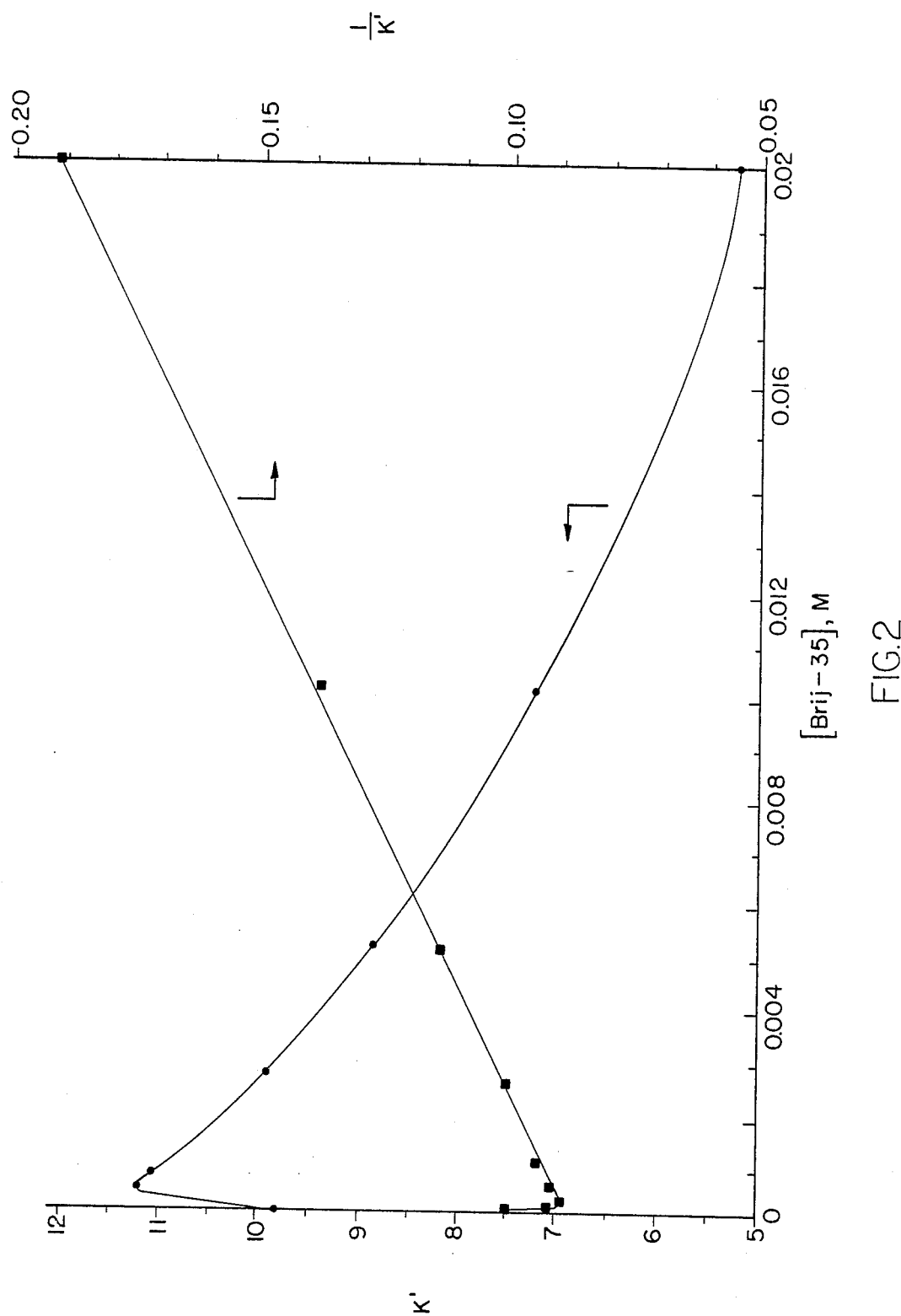
FIG. 2 is a chart illustrating the dependence of k' and 1/k' on the concentration of Brij-35 for chloramphenicol.

This example was conducted in accordance with the procedure in Example 1, except that the sample was 10 μg/ml of chloramphenicol. FIG. 2 illustrated the elution behavior of chloramphenicol. A sharp change in $k'$ occurs at approximately 0.00025 M Brij-35, indicating that the surfactant was undergoing micellization. Assuming that the 0.00025 M value is equal to the critical micelle concentration (CMC), the solute-micelle equilibrium constants can be calculated from the slope/intercept of the plot of $1/k'$ versus $[M_m]$.

EXAMPLE 3

This example was conducted in accordance with the procedure in Example 1, except that the flow rate was 1.0 ml/min. and a 20 μl sample of serum blank (A), a 20μl sample of serum with 20 μg/ml chloramphenicol (B) and a 20 μg/ml sample of chloramphenicol in water (C) were injected into the chromatographic column. FIG. 3A showed the elution behavior of serum blank, where most serum components elute at the solvent front. FIGS. 3B and 3C showed the chromatograms using a Supelcosil CN column of 20 μg/ml chloramphenicol dissolved in a serum matrix and in distilled water, respectively, both eluted in approximately 15 minutes. The resolution in the serum medium was sufficient to quantitatively determine chloramphenicol, and the sensitivity was adequate to monitor the normal therapeutic range in serum (10–20 μg/ml). The peak heights of the drug in FIGS. 3B and 3C are equal, indicating that the protein-bound drug was completely displaced by the surfactant monomers and/or micelles in the mobile phase.

EXAMPLE 4

This example was conducted in accordance with the procedure in Example 1, except that SDS with 10% propanol was used as the surfactant in the preparation of the mobile phase, fluorescence detection was employed, and a C-18 chromatographic column was used.

Further, the flow rate was adjusted to 1.0 ml/min. and a 20 μl sample of urine blank and a 20 μl sample of urine with 40 ng/ml propanolol and 400 ng/ml quinidine were injected into the chromatographic column. FIG. 4A shows a chromatogram of the urine blank and FIG. 4B shows a chromatogram of the urine blank containing 40 ng/ml propanolol and 400 ng/ml quinidine.

EXAMPLE 5

Figure 5A:
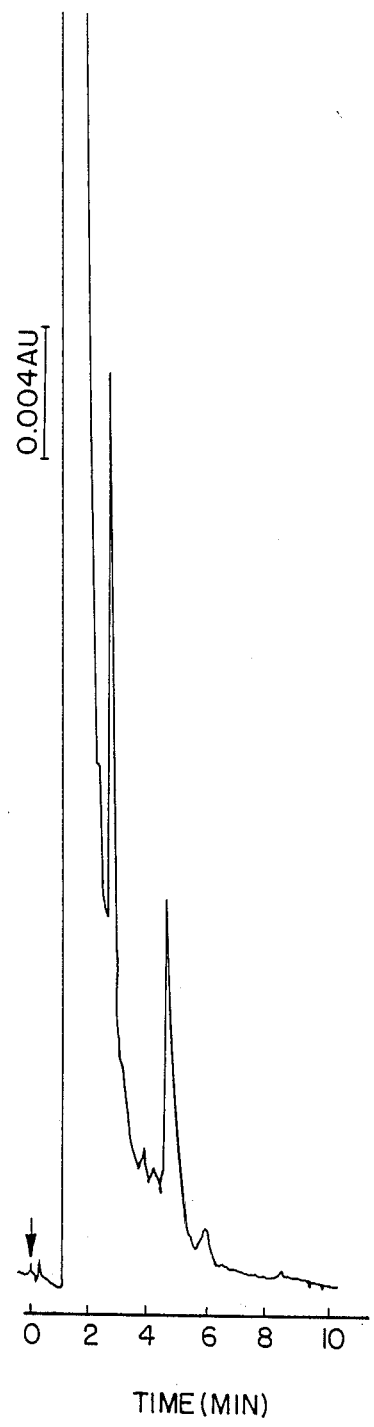
FIGS. 5A and 5B are chromatograms of serum blank (A), and serum with acetaminophen, phenobarbital, and chloramphenicol (B), respectively.
Figure 5B:
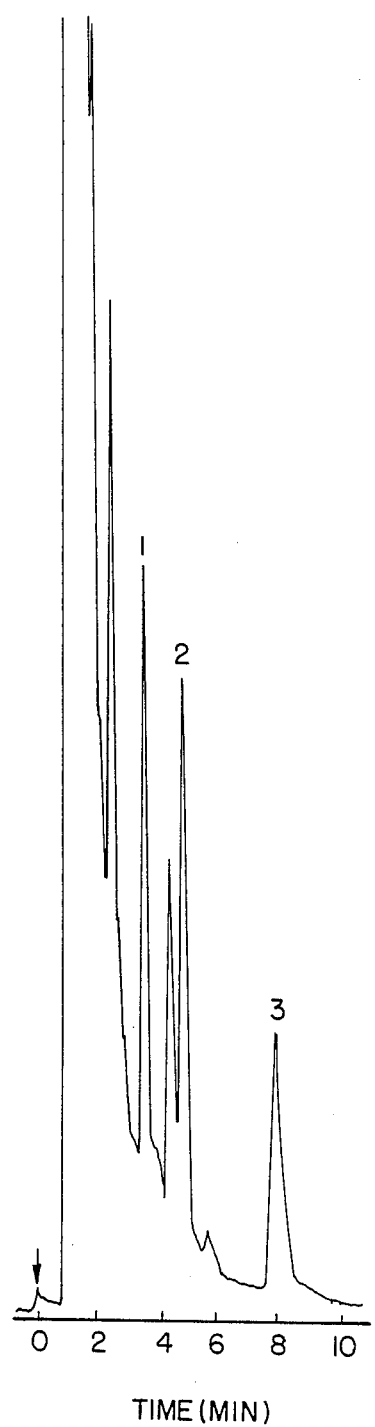

This example was conducted in accordance with the procedure in Example 1, except that SDS was used as the surfactant in the preparation of the mobile phase and the flow rate was adjusted to 1.0 ml/min. A 2.5 μg/ml sample of acetaminophen, a 15 μg/ml sample of phenobarbital, a 10 μg/ml sample of chloramphenicol in serum (B) and a serum blank (A) were injected into the chromatographic column. FIG. 5B illustrates the chromatogram of serum containing acetaminophen (1), phenobarbital (2), chloramphenicol (3) and FIG. 5A illustrates the chromatogram of the serum blank.

EXAMPLE 6

Figure 6A:
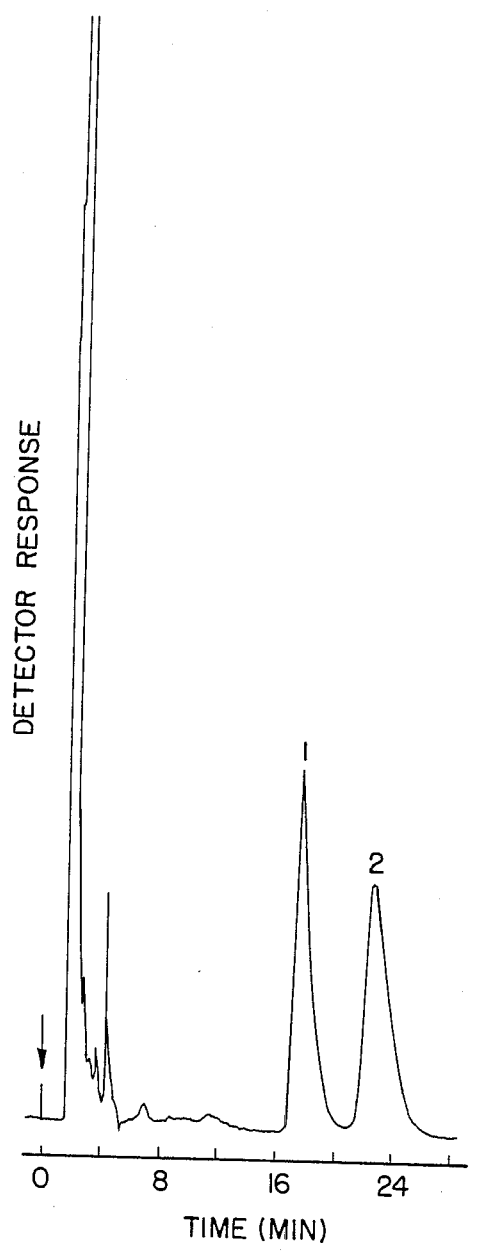
FIGS. 6A and 6B are chromatograms of quinine (1) and quinidine (2) using two different wavelength filters.
Figure 6B:
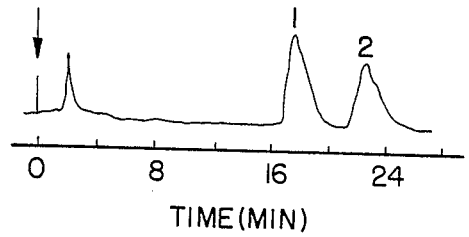

This example was conducted in accordance with the procedure in Example 1 except that sodium dodecyl sulfate with 10% propanol was used as the surfactant in the preparation of the mobile phase, fluorescence detection was employed with different emission wavelength cut-off filters, and the flow rate was adjusted to 1.0 ml/min. Serum blanks with 2 μg/ml of added quinine and 2 μg/ml of added quinidine were injected into the chromatographic column. FIGS. 6A and 6B illustrate the chromatograms for quinine (1) and quinidine (2). The The two solutes were eluted at the same time at all concentrations, but with the addition of 10% propanol resulted in better baseline separation. This indicated that propanol enhanced sensitivity by improving efficiency and selectivity. Furthermore, the fluorescence signal of the early eluting components was virtually eliminated by changing the emission wavelength cutoff filter from 300 nm (FIG. 6A) to 470 nm (FIG. 6B).

Obviously, other modifications and variations of the present invention are possible in the light of the above teachings. It is, therefore, to be understood that changes may be made in the particular embodiments of this invention which are within the full intended scope of the invention as defined by the appended claims.

What is claimed is:

1. A method for a determination of a concentration of drugs in bodily fluids which consists essentially of:
   (a) injecting a bodily fluid containing a drug into a chromatographic column wherein the mobile phase is anionic, cationic, zwitterionic, or nonionic surfactant micelles at a concentration at or above the critical micelle concentration of said surfactant;
   (b) eluting said bodily fluid and said mobile phase from said chromatographic column; and
   (c) detecting said drug in the bodily fluid eluting from said column to produce a chromatogram proportional to the concentration of said drug.

2. A method as defined in claim 1, wherein said bodily fluid is serum.

3. A method as defined in claim 1, wherein said bodily fluid is urine.

4. A method as defined in claim 1, wherein said surfactant is sodium dodecyl sulfate.

5. A method as defined in claim 1, wherein said surfactant is polyoxyethylene dodecyl.

6. A method as defined in claim 1, where in step (a) the anionic or nonionic surfactant is at a concentration of about 1.01 times the critical micelle concentration to about 0.99 times the Krafft point.

7. A method as defined in claim 1, where in step (a) the bodily fluid is injected at a flow rate effective to provide in step (b) a flow rate from said column of about 10 μl/min. to about 20 ml/min.

8. A method as defined in claim 1, wherein propanol is added to the mobile phase in a range of above 0% to about 40% of the volume of the mobile phase.

9. A method as defined in claim 1, wherein the pH of the mobile phase is adjusted to a range of aobut 2 to about 7.

10. A method as defined in claim 1, wherein said bodily fluid is saliva, peritoneal fluid, cerebrospinal fluid, blood plasma, sweat, semen, feces, mucous-containing fluid, tears, vaginal whole blood, embryonic fluid.

11. A kit useful for a determination of a drug concentration in a bodily fluid which consists essentially of:
   a carrier having vertical sides, a bottom affixed to said sides and a multiplicity of compartments each including surfactant as a component for preparation of a mobile phase for chromatographic analysis;
   a second container means including a solvent for adding to the surfactant for preparation of a mobile phase;
   a third container means including known drug standards in an appropriate body fluid at predetermined values for standardization of a chromatographic column;
   a fourth container means including an appropriate body fluid containing no drugs for calibration of the chromatographic column;
   a fifth container means including appropriate organic modifiers for preparation of a mobile phase;
   a sixth container including appropriate inorganic modifiers for preparation of a mobile phase;
   a seventh container means including pH adjustment materials; and
   a packet with instructions for preparation of the mobile phase and calibration of the chromatographic column for determination of the concentration of the drug.

12. A kit of claim 11, containing an eighth container means including a chromatographic column.

* * * * *